United States Patent [19]

Shimada et al.

[11] 4,258,319
[45] Mar. 24, 1981

[54] SURFACE DEFECT DETECTING APPARATUS FOR USE WITH ROTATING CIRCULARLY SHAPED METALLIC MATERIAL

[75] Inventors: Katsuhiko Shimada, Yokohama; Isamu Komine, Yokosuka; Hideya Tanabe, Yokohama; Shuichi Tsunozaki, Yokohama; Masayoshi Yamada, Yokohama; Tsuguo Takahashi, Tokyo, all of Japan

[73] Assignee: Nippon Kokan Kabushiki Kaisha, Tokyo, Japan

[21] Appl. No.: 940,155

[22] Filed: Sep. 5, 1978

[30] Foreign Application Priority Data

Sep. 8, 1977 [JP] Japan .............................. 52-107197

[51] Int. Cl.³ ..................... G01N 27/72; G01R 33/00; G01N 27/82; G01R 33/12
[52] U.S. Cl. .................................... 324/226; 324/225; 324/237; 324/242; 324/262
[58] Field of Search ............... 324/225, 226, 228, 234, 324/236–243, 262

[56] References Cited

U.S. PATENT DOCUMENTS

| | | | |
|---|---|---|---|
| 2,253,211 | 7/1944 | Zuschlag | 324/238 |
| 3,244,972 | 4/1966 | Fisher | 324/226 |
| 3,271,662 | 9/1966 | Quittner | 324/233 |
| 3,675,118 | 7/1972 | Booth | 324/226 |

OTHER PUBLICATIONS

Hoffman, "A New Rotating-Probe Eddy Current Method for Inspecting Bar Surface", 10/1975, Materials Evaluation, vol. 33, No. 10, pp. 237–242.

*Primary Examiner*—Gerard R. Strecker
*Assistant Examiner*—Walter E. Snow
*Attorney, Agent, or Firm*—Haseltine and Lake

[57] ABSTRACT

The surface defect detecting apparatus for rotating cylindrical metal pieces which move in a lengthwise direction relative to a sensor block, has a plurality of eddy-current flaw detecting coils facing the test piece. The sensor block rotates about a horizontal axis extending vertically with respect to the axis of the test piece to follow up deflections of the test piece in the direction of the axis of rotation. Front and rear ends of the sensor block, have a pair of guide wheels that engage the piece; also present are color marking nozzles for marking defective areas in response to detector signals. Relative movement in the longitudinal direction of the test piece is carried out by means of a carriage carrying the sensor block. Each guide wheel is spaced from another in a plane transverse to the longitudinal direction of the test piece. A number of coils with designated impedances are connected to a generator and are disposed in longitudinal direction of the test piece in a single sensor holder within the sensor block. The holder has turning wheels at front and rear ends thereof in a longitudinal direction of the test piece, and are each positioned between the guide wheels in a direction for spiral scanning, and in rotatable contact with the outer surface of the test piece. Impedances of the coils are selected to allow feedback amplifiers to form a feedback circuit with two of the coils and are linear for eddy-current signals corresponding to different flaw depth ranges. Signals of a detector unit associated with different flaw depth range are amplified within the linear characteristic range and supplied to nozzles which spray different colors depending on flaw depth.

1 Claim, 8 Drawing Figures

FIG.2
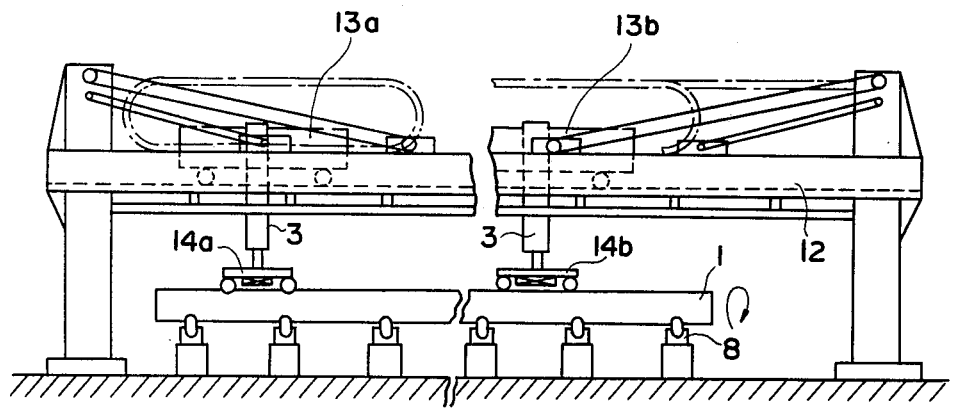
FIG.6
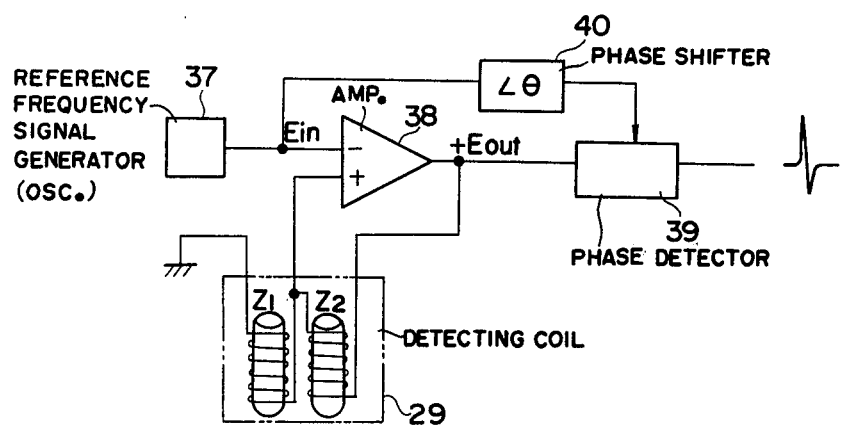
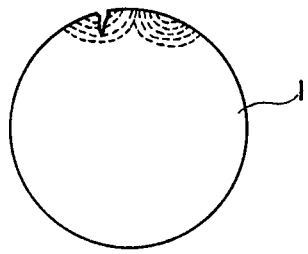

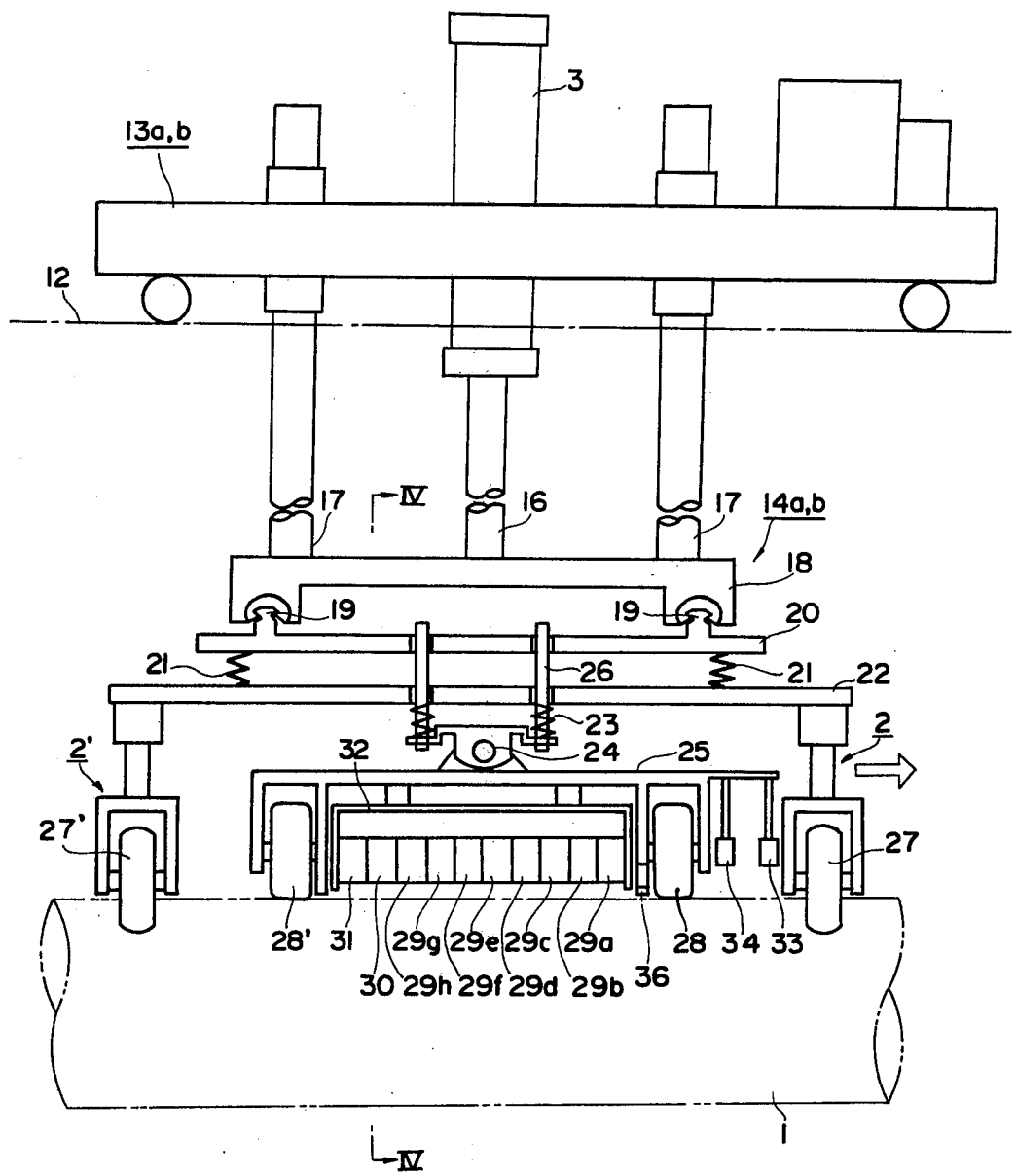

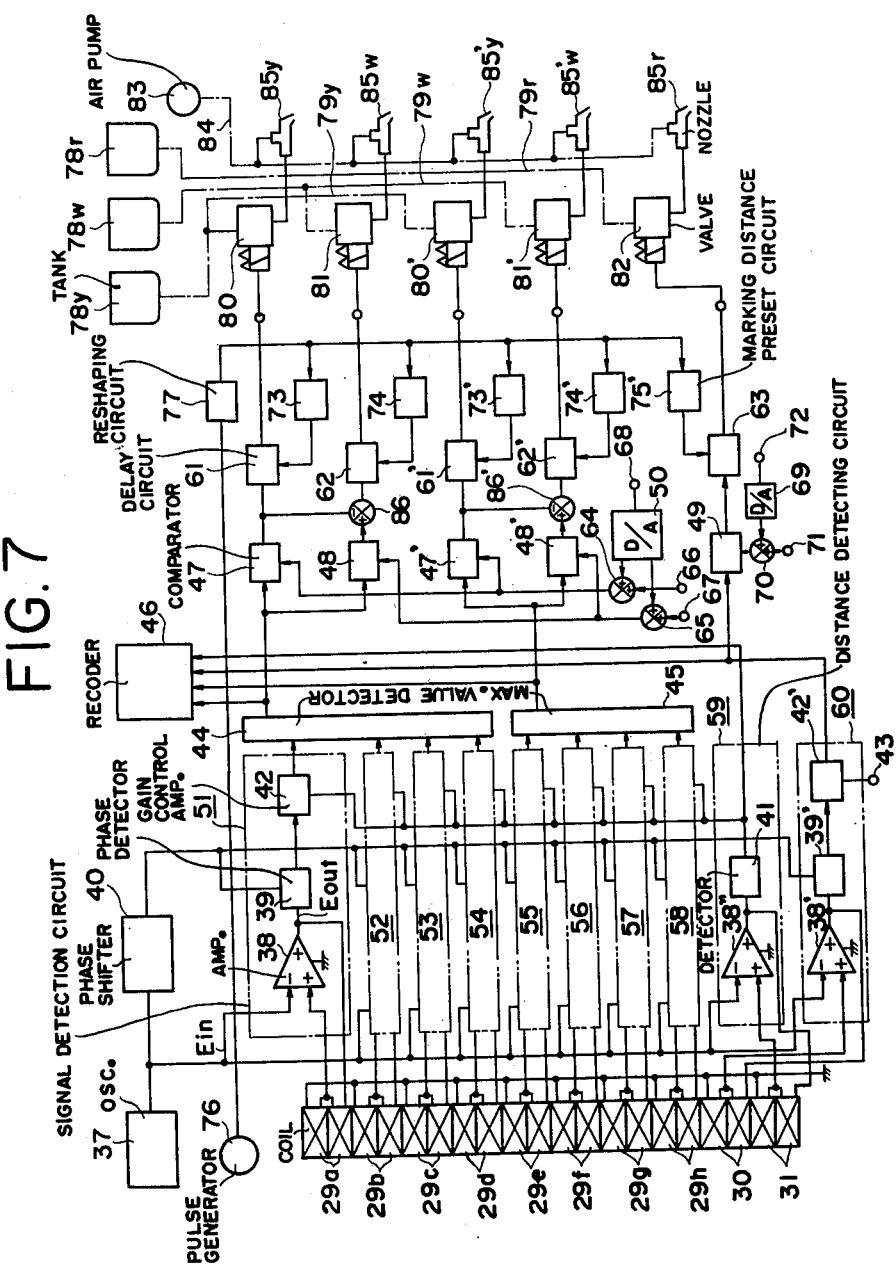

SURFACE DEFECT DETECTING APPARATUS FOR USE WITH ROTATING CIRCULARLY SHAPED METALLIC MATERIAL

BACKGROUND OF THE INVENTION

The present invention relates to a surface defect detecting apparatus for use with metallic materials having a circular external shape, such as, steel round billets, round bars or steel pipes.

Among the automatic flaw detecting apparatus heretofore known in the art for detecting the surface defects of round billets, are those which are called as magnetic flaw detecting apparatus. Though this type of flaw detecting apparatus has the advantage of automatic flaw detection over the known magnetic particle flaw detection method, there is a disadvantage that since magnetic flux is passed from an electromagnet through a rotating round billet and the resulting leakage flux from a defective area is detected by sensors such as magnetism responsive diodes, the sensors must be arranged in close proximity to the surface of the round billet with a very small gap of the order of 0.2 mm, with the result that the presence of projections or ovals on the round billet makes it impossible to effect the detection and consequently the outer surface of the billet must be preliminarily be prepared. Another disadvantage is that since each sensor is provided with a shoe which contacts with the round billet surface to maintain the very small gap, the oxide particles on the billet surface tend to deposit in the very small gap at the shoe or the gap between the diode surface and the round billet surface, thus producing ill effects on the detection function. Still another disadvantage is that since the sensors are semiconductor devices, the sensors are easily affected by heat and they are not able to detect defects in a heated round billet without cooling means. Still further disadvantage of the magnetic flux leakage detection method is that if the depth of flaws is greater than about 2 mm, for example, the amplitude of the outputs becomes constant thus making it impossible to discriminate the size of the defects, and moreover if part of the coils for applying flux to the round billet deviate from the billet end, the detection characteristic is changed and a portion of the round billet end corresponding to the diameter of the magnetic flux coil fails to be subjected to the flaw detection, the portion usually amounting as much as about 40 mm.

On the other hand, the defect areas detected automatically by a surface defect detecting apparatus of the type described above or any other suitable surface defect detecting apparatus are removed at the next processing step to produce round billets having no surface defects which in turn are used as raw material for producing a variety of products, and consequently the location of the detected defects must be accurately marked for the defect removing operation. In the past, it has been the usual practice to effect this type of marking by reinstating the recorded data of the inspection results in the round billet by an operator and consequently there is a problem of inefficiency for the operations including from the separation of reject material according to the degree of defects up to the operation of removing the defects by cutting.

SUMMARY OF THE INVENTION

The present invention has been made in view of these circumstances, and it is a primary object of the invention to provide a surface defect detecting apparatus in which a plurality of eddy-current flaw detecting coils are used in combination with feedback amplifiers to linearize their input-output characteristics and the presence of surface defects is detected by a change in the impedance of the coils, thus forming a relatively large gap between the sensors and the surface of a material to be inspected and thereby overcoming the previously mentioned deficiencies in the prior art.

It is another object of the invention to provide such surface defect detecting apparatus which is capable of simultaneously effecting the detection of defects and the making of defective areas in accordance with the degree of defects.

In accordance with a basic form of the present invention, there is thus provided a surface defect detecting apparatus comprising a sensor block adapted for movement in the lengthwise direction of a material to be inspected in the form of a round or cylindrical metallic material rotated at a predetermined peripheral speed so as to spirally scan the outer surface of the material at a predetermined feed width, the sensor block being supported on a carriage movable in the lengthwise direction of the material and including a pair of guide wheels at each of the front and rear parts thereof in the direction of movement, each pair of guide wheels being spaced away and directed in the spiral scanning direction for rotation by the rotation of the material in contact with its outer surface, the sensor block further including a coil holder disposed middle of the front and rear guide wheel pairs and holding a plurality of eddy-current flaw detecting coils longitudinally arranged in a line in the direction of movement to face the outer surface of the material with a predetermined gap therebetween, the coil holder including a turning wheel provided at each of its front and rear parts in the direction of movement and directed in the spiral scanning direction so as to be rotated by the rotation of the material in contact with its outer surface and maintain the predetermined gap between the coils and the material.

In accordance with another form of the invention, there is provided a surface defect detecting apparatus comprising, in addition to the above-mentioned basic construction, a first table unit for end locating purposes whereby a material entered for flaw detection is moved axially to locate its one end in a predetermined position, a second table unit including turning rollers for rotating the material subjected to the end positioning at a predetermined peripheral speed, a supporting girder unit for movably hanging and supporting the carriages so that the sensor blocks suspended from the carriages are held in position just above the second table unit, and an extractor disposed to be movable to cross the first and second table units at right angles to introduce the material onto the first table unit, transfer the material from the first table unit onto the second table unit and remove the material from the second table unit.

In accordance with still another form of the invention, the surface defect detecting apparatus further comprises speed setting means whereby in accordance with a flaw detecting width or pitch determined by the size of the eddy-current flaw detecting coils, a predetermined set peripheral speed value and the outer diametral dimension of a material to be inspected, the travel speed of the carriages is determined so as to ensure that the entire outer surface of the material is subjected to spiral flaw detection at the flaw detecting width.

In accordance with still another form of the invention, each of the sensor blocks further includes a separate eddy-current distance detecting coil for measuring the gap between the eddy-current flaw detecting coils and the outer surface of the material, and there is further provided a compensation circuit for performing automatic gain control on the detection signals generated by the eddy-current flaw detecting coils in response to the gap distance signal generated by the distance detecting coil.

In accordance with still another form of the invention, a plurality of nozzles are mounted on each sensor block whereby a marking paint is sprayed to the location of a defect in accordance with the detection output signal of each eddy-current flaw detecting coil. Where a signal processing circuit is provided for each of the plurality of eddy-current flaw detecting coils to give a different flaw detecting characteristic to each coil so as to discriminate the size of defects in a plurality of ranges, a plurality of nozzles may be mounted on each sensor block so that marking paint of different colors are selectively sprayed in response to flaw detection output signals of different levels corresponding to the different ranges of the defects. In the latter case, each sensor block supports a plurality of eddy-current flaw detecting coils arranged in a line to separately generate a flaw detection output and the flaw detecting coils are formed into groups each including at least one of the coils, whereby a plurality of marking nozzles are mounted on the sensor block along the raw of the flaw detecting coils at positions corresponding to the respective coil groups to respond to the flaw detection output thereof and spray marking paint to a detected defective area after a predetermined delay time independently of one another.

Where a plurality of marking nozzles are provided at positions corresponding to a plurality of flaw detecting coil groups, the detection outputs of the flaw detecting coils in the groups may be discriminated in accordance with a plurality of different sizes of defects in common to the respective groups so as to cause the plurality of nozzles to spray the paint of different colors in accordance with the different sizes of defects. Alternatively, the raw of flaw detecting coils may include at least one large flaw detecting coil having for example a preset detection sensitivity to detect the defects in the material which are greater than a predetermined size, and a separate marking nozzle may be mounted on the sensor block to spray paint of a different color only in response to the detection output of the exclusive large flaw detecting coil.

Thus, the apparatus of the invention has among its great advantages the fact that the desired flaw detection can be effected all over the surface of a round billet having ovals without damaging the flaw detecting coils, that the use of the eddy-current flaw detection method has the effect of reducing the size of the coils and ensuring a flaw detecting characteristic having a wide linearity even at a distance of for example about 5 mm from the billet surface to the coils thus allowing the use of the sensors using no semiconductor devices but comprising only the coils and thereby making it possible to effect the desired flaw detection even in the case of round billets of over 80° C., that the depths of defects can be separated into a plurality of ranges to automatically effect the corresponding markings, that the size of defects can be discriminated in a plurality of ranges to effect automatically the corresponding markings in different colors at the accurate defective areas during flaw detecting operation, and that upon completion of the flaw detection, as for example, the billets with a large flaw marking can be readily determined and sorted as reject product which cannot be subjected to flaw removing operations and the billets with medium and small flaw markings can be easily subjected to flaw removing operations in which a grinder is for example pressed against the marked areas of the surface to remove the defects, thus ensuring a greatly improved efficiency for the flaw detection and flaw removing operations.

The above and other objects, features and advantages of the invention will become more apparent from the following detailed description taken in conjunction with the accompanying drawings.

BRIEF DESCRIPTION OF THE DRAWINGS

FIG. 2 is a partly cutaway front view of the apparatus shown in FIG. 1.

FIG. 3 is an enlarged front view of a sensor block.

FIG. 6 is a basic flaw detecting circuit diagram.

FIG. 7 is a block circuit diagram showing an embodiment of a signal processing system for the flaw detecting apparatus.

DESCRIPTION OF THE PREFERRED EMBODIMENTS

Figure 1:
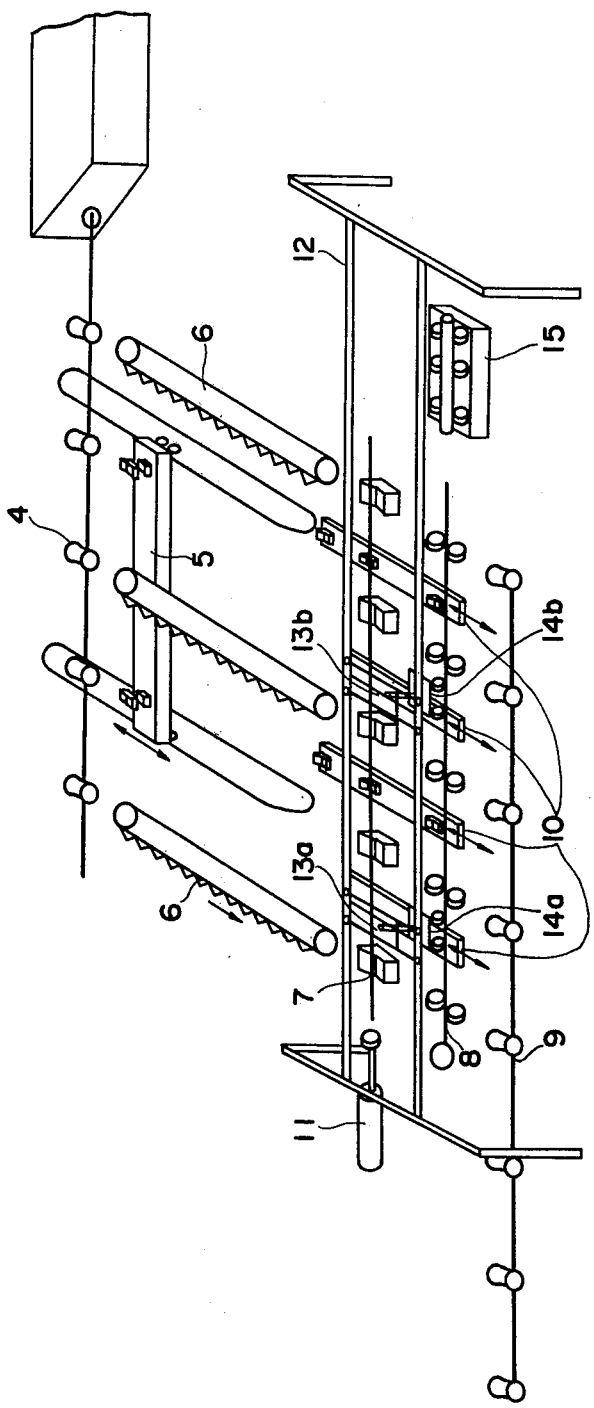
FIG. 1 is perspective view showing a surface defect detecting apparatus according to an embodiment of the invention.

Referring first to FIGS. 1 and 2, numeral 4 designates a preceding processing unit or shot blast rear table connected to a flaw detecting apparatus by way of a rope transfer 5 and a chain transfer 6.

The flaw detecting apparatus includes an end positioning table unit 7 and a turning roller table unit 8 which are arranged in parallel to each other, and the apparatus further includes a flaw detection rear table 9 arranged in parallel and connected to the following processing equipment, e.g., a grinding equipment. The apparatus further includes an extractor 10 which is movable in a direction at right angles to the table units 7, 8 and 9, whereby the round billets moved in a transverse direction by the chain transfer 6 are moved, one at a time, onto the end positioning table unit 7 from which the billet is moved onto the turning roller table 8 and further onto the rear table 9. The end positioning table unit 7 includes a hydraulic cylinder piston unit 11 whereby one end of a billet 1, upon entering the table unit 7, is pushed and located in a predetermined position. Installed above the turning roller table unit 8 is a supporting girder unit 12, and two carriages 13a and 13b are movably hanged on the girder unit 12. Sensor blocks 14a and 14b are respectively suspended from the carriages 13a and 13b so as to be raised and lowered by pressure units or hydraulic cylinder-piston units 3 just above the turning roller table unit 8. Disposed on the extension of the turning roller table unit 8 and within the extent of the girder unit 12 is a calibration turning roller unit 15 which calibrates the sensor characteristics.

With the illustrated embodiment, the two carriages 13a and 13b are suspended from the supporting girder unit 12 and their sensor blocks 14a and 14b respectively inspect for defects the halves of the length of the round billet 1 with a small amount of overlapping, thus reducing to half the time required for inspecting the entire length of the billet 1 for defects. In the Figures, the left end of the round billet 1 is located in the predetermined position by the end positioning table unit 7 and simultaneously its length is measured. Then, the extractor 10 moves the round billet 1 parallely onto the turning roller table unit 8 where the billet 1 is rotated at a predetermined constant peripheral speed. The supporting girder unit 12 includes a position sensor, e.g., limit switch (not shown) at a position corresponding to the predetermined end position as well as at each of a plurality of middle points, whereby the carriage 13a is stopped at the predetermined left end position detected by the corresponding position sensor and the other carriage 13b is stopped at a position which is deviated to the left by an amount corresponding to a predetermined overlap from the central position detected by one of the position sensors at the plurality of middle points which is selected in accordance with the result of the previous measurement of the length, thus placing the carriages 13a and 13b in condition for initiating flaw detection. In this ready condition, the sensor blocks 14a and 14b respectively suspended from the carriages 13a and 13b are brought into contact with the surface of the round billet 1, and the end of the round billet 1 is inspected for defects by its rotation over one revolution to reduce the uninspected end portion. Thereafter, the outer surface of the round billet 1 is spirally scanned entirely as the carriages 13a and 13b are moved to the right.

Figure 4:
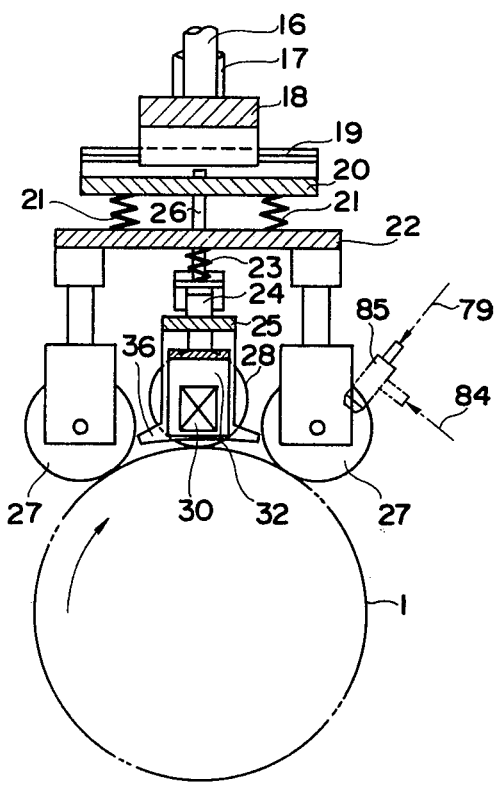
FIG. 4 shows the sensor block looked in the direction of the arrow line IV—IV of FIG. 3.

Each of the sensor blocks is constructed as shown in FIGS. 3 and 4, that is, it comprises a base member 18 which is suspended from the carriage by a vertically movable press shaft 16 coupled to the piston rod of a hydraulic cylinder-piston unit 3 and attached to the carriage and guide shafts 17 for vertically guiding the base member 18 relative to the carriage, and attached to the base member 18 is a slide base plate 20 which is slidable in a horizontal direction vertical to the direction of travel of the carriage by means of sliders 19 so as to cause the base member 18 to follow the oscillation of the round billet 1 due to it bend. A follow-up base plate 22 is suspended from the slide base plate 20 by means of coil springs 21, and a sensor holder 25 is suspended from the base plate 22 by means of another springs 23 (volute springs) by way of a hinge 24. In other words, the sensor holder 25 is rotatable about the hinge 24 in a plane along the direction of travel of the carriage relative to the base member 18. The coil holder 25 is further adapted to receive the pressing force applied by the vertically movable press shaft 16 through the springs 21 and 23. Disposed inside the sensor holder 25 are a plurality of eddy-current flaw detecting coils 29a, 29b, 29c, 29d, 29e, 29f, 29g, 29h and 30 and a distance detecting coil 31 which are arranged in a line in the direction of movement by the carriage or in the lengthwise direction of the round billet 1 and held in place to face downward, and consequently the lower surface of each coil is opposite to the outer surface of the round billet 1 with a predetermined gap therebetween. As a result, by virtue of the rotation of the round billet 1 and the movement in the lengthwise direction of the round billet 1 of the sensor block 14a or 14b caused by the carriage, the surface of the round billet 1 will be spirally scanned by the coils 29a to 29h and 30 at a pitch corresponding to the total widthwise dimension of these coils. Shafts 26 are guide shafts which are secured at their lower ends to the hinge 24 and slidably extended through the base plates 20 and 22.

Mounted respectively to the front and rear parts of the base plate 22 are two pairs of follow-up guide wheels 27 and 27' which are respectively arranged on both sides of the direction of movement so as to be spaced away from each other, and in this way each pair of the guide wheels are pressed against the sides of the outer surface of the round billet 1 with its top interposed between the wheels as shown in FIG. 4. A pair of turning wheels 28 and 28' are respectively mounted to the front and rear parts of the sensor holder 25 positioned inside the area enclosed by the four guide wheels 27 and 27', and in this way the dimension of the gap between the lower surface of the interposed eddy-current flow detecting coils 29a to 29h and 30 and the distance detecting coil 31 and the surface of the round billet 1 is maintained at a predetermined value of 5 mm, for example. These coils are fixedly mounted to the sensor holder 25 by means of a holder 32 made of a nonmagnetic material, and proximity switches 33 and 34 are also mounted at a predetermined spacing to the front part of the sensor holder 25 so as to detect the position of the round billet end.

Figure 5A:
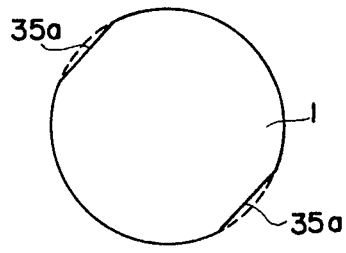
FIGS. 5a and 5b are end views showing the ovals on round billets.
Figure 5B:
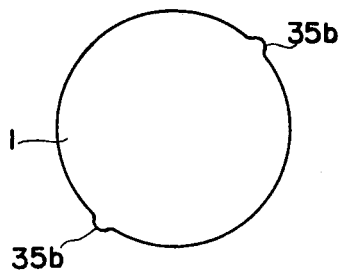

As shown in FIG. 5, the round billet 1 usually includes concave ovals 35a or convex ovals 35b, so that when the oval approaches the lower part of the coils by the rotation of the round billet 1, with the sensor block described above the turning wheels 28 and 28' of the holder 25 follow up the oval and consequently the gap below the coils is maintained at a constant value, thus preventing the oval projections from damaging the coils and always maintaining the gap between the coils and the billet outer surface at the constant value with the resulting prevention of any change in the detection characteristics.

Also provided at the end of the holder 25 located on the side of the round billet end, is a protector 36 which projects beyond the lower surface of the coils and positioned above the lower end of the turning wheel so as to protect the coils from being damaged by the edge of the billet end in the event that the turning wheel 28 falls off the round billet end.

The first and second proximity switches 33 and 34 are provided to detect the round billet end prior to the coils, and the sequence is determined so that the carriage travel speed is decreased in response to the detection of the billet end by the first proximity switch 33, the travel speed is further decreased, and then when the billet end is detected by the second proximity switch 34, after a predetermined delay the movement of the carriage is stopped with the turning wheel 28 being located at the billet end.

FIG. 6 shows the basic construction of a flaw detecting circuit in which a reference frequency signal generator 37 applies an AC signal to an eddy-current flaw detecting coil 29 through an amplifier 38 to produce eddy-currents in a round billet, whereby a change in the eddy currents associated with a defect is detected as a change in the coil impedance and a flaw detection output signal is generated from a phase detector 39. In the Figure, numeral 40 designates a phase shifter for generating synchronizing signals for phase detection purposes. In this case, if $E_{in}$ represents the input voltage or reference signal to the amplifier 38 and $Z_1$ and $Z_2$ represent the impedance of the two coil elements constituting the flaw detecting coil, the resulting output signal $E_{out}$ is given by $$E_{out} = E_{in} \cdot \frac{G}{1 - G \cdot \frac{Z_1}{Z_1 + Z_2}}$$

where G is the gain of the amplifier 38. By suitably selecting the value of the coil impedances $Z_1$ and $Z_2$ under the reference condition, it is possible to change the feedback ratio of the circuit, and also by changing the amplification degree of the amplifier 38 and the flaw detecting phase, it is possible to change the range in which an output having a good linearity with respect to the depth of defects can be produced. As a result, by selecting the flaw detecting coils 29a to 29h as small and medium flaw coils which show the desired linearity for all defects which are 5 mm deep or smaller and selecting the flaw detecting coil 30 as a large flaw coil which shows the desired linearity for defects over 5 mm deep, it is possible to discriminate the degree of defects. Further, since the coil shape changes this characteristic, the large flaw coil alone may be increased in shape.

With the circuit of FIG. 6, the distance detecting coil 31 is connected to a distance detecting circuit which performs linear detection instead of phase detection and its output is used as a control signal in an automatic gain control amplifier circuit (an AGC circuit) following the detector output in the Figure.

With the embodiment shown in FIG. 3, if the coils 29a to 29h each has a width of 18 mm or a total width of 144 mm and if the (flaw detecting pitch) distance of travel of carriage 13a,13b, during one revolution of billet is selected as 135 mm or the flaw detecting lap percentage is selected (144−135)/144=0.06 (6%) and the peripheral speed for the rotation of the round billet by the turning rollers is held constant at 500 mm/sec, the carriage travel speed V is determined by the round billet outer diameter d (mm), and Vr, is the rotational speed of billet as shown by the following equation $$V = \frac{135 \cdot Vr}{\pi d} = \frac{21496 \cdot 8}{d}$$

V is so determined as to be in inverse proportion to d. Although not shown, the carriage drive unit includes a control unit whereby the carriage travel speed is controlled automatically according to this equation by establishing the outer diameter of the billet entered.

As shown in FIG. 4, each of the sensor blocks 14a and 14b is provided with marking paint spraying nozzles 85 which are for example supported by the holder 25 in such a manner that each nozzle is directed to the round billet surface delayed a predetermined distance from just below the coil with respect to the direction of rotation of the round billet. This predetermined distance is determined in accordance with the peripheral speed of the billet rotated by the turning rollers, and it is so designed that the area detected by the coil arrives just below the nozzle after a certain delay time in the signal system and the working system. For example, it may be arranged so that when a defect is detected by any of the coils 29a to 29b, white paint is sprayed from the nozzle mounted in a position corresponding to the coil, and when a defect is detected by the large flaw coil 30, red paint is sprayed from another nozzle mounted in a position corresponding to the coil 30. In FIG. 4, a pipe line 79 connected to the nozzle 85 is a paint line, and a pipe line 84 is a compressed air line. Although not shown, a paint tank and a pump are connected through a solenoid valve to the paint line 79, and a compressed air source is connected to the air line 84 thus allowing the air line 84 to serve an additional function of always blowing air and removing dust and the like on the outer surface of round billets. The solenoid valve is actuated by a flaw signal detected by the coil so that paint is supplied to the nozzle and the paint is sprayed from the nozzle at the instant that the detected defect area arrives just below the nozzle.

FIG. 7 shows the construction of a more elaborate flaw detecting circuit, and basically describing its operation with respect to the eddy-current flaw detecting coil 29a there is provided a flaw signal detection circuit 51 in which an AC signal is applied to the coil 29a through an amplifier 38 from an oscillator 37 for generating a reference frequency signal to produce eddy-currents in a round billet, whereby a change in the eddy-currents caused by a defect is detected as a change in the coil impedance and a flaw signal is generated through a phase detector 39 and an automatic gain control amplifier 42. In the Figure, numeral 40 designates a phase shifter for generating synchronizing signals for the purpose of phase detection, and 52 to 58 and 60 flaw signal detection circuits which are respectively associated with the coils 29b to 29h and 30 and identical in construction with the previously mentioned circuit 51. In this case, if $E_{in}$ represents the input signal or reference signal to the amplifier 38 and $Z_1$ and $Z_2$ designate the coil impedance of the two coil elements constituting the coil, then the output signal $E_{out}$ is given by the following equation as mentioned previously.

$$E_{out} = E_{in} \cdot \frac{G}{1 - G \cdot \frac{Z_1}{Z_1 + Z_2}}$$

where G is the gain of the amplifier 38. By suitably selecting the value of the coil impedances $Z_1$ and $Z_2$ under the reference condition it is possible to change the feedback ratio of the circuit, and by changing the amplification degree of the amplifier 38 and the flaw detection phase it is possible to change the range in which an output with a good linearity with respect to the depth of defects can be obtained. As a result, with the case shown in FIG. 7, by selecting the flaw detecting coils 29a to 29h as small and medium flaw coils which show the desired linearity for all defects 5 mm deep or smaller and selecting the flaw detecting coil 30 as a large flaw coil which exhibits the desired linearity for defects over 5 mm deep, it is possible to discriminate defects of large size. In this connection, the coil shape also changes this characteristic and consequently the large flaw coil alone may be increased in size.

In the circuit of FIG. 7, the distance detecting coil 31 is connected to a distance detecting circuit 59 comprising a feedback amplifier 38″ and a detector 41 which performs linear detection in place of phase detection, and the output of the detector 41 is used as a gain control signal in the automatic gain control amplifiers 42 (AGC circuits) following the output of the respective phase detectors in FIG. 7. In the Figure, a large flaw detecting circuit 60 comprises the similar feedback amplifier 38′ and phase detector 39′ and an AGC amplifier 42′, and the AGC amplifier 42′ alone is subjected to automatic gain control in response to a separately applied preset input 43.

In the Figure, numerals 85y and 85′y designate marking nozzles for spraying medium flaw marking yellow paint, 85w and 85′w marking nozzles for spraying small flaw marking white paint, and 85r a marking nozzle for spraying large flaw marking red paint. The nozzles 85y and 85w are mounted on the sensor block so as to be adjacent to each other and placed in positions corresponding to the coils 29a, 29b and 29c, 29d, respectively, as in the case shown in FIG. 4, and in the like manner the nozzles 85′y and 85′w are mounted on the sensor block in positions corresponding to the coils 29e, 29f and 29g, 29h, respectively, and the nozzle 85r is mounted on the sensor block in a position corresponding to the coil 30.

In the Figure, numeral 76 designates a pulse generator for measuring the peripheral speed of a round billet and its output pulses has a period corresponding to the peripheral speed of the round billet.

Each nozzle sprays the paint at the instant that the defect area detected by the associated coil arrives just below the nozzle after a delay time in the signal system and the working system.

As regards the outputs of the respective flaw signal detecting circuits, the outputs of the detecting circuits 51 to 54 are applied to a maximum value detecting circuit 44 (analog OR circuit) and the outputs of the detecting circuits 55 to 58 are applied to another similar maximum value detecting circuit 45, thus providing two channels for the two groups each including the four small and medium flaw coils. The maximum value detecting circuits 44 and 45 each generates an output which is the flaw signal having the highest amplitude among the input signals, and their outputs are respectively branched and applied to medium flaw comparison circuits 47 and 47′ and to small flaw comparison circuits 48 and 48′. These comparison circuits compare the amplitude of flaw signal inputs with a reference medium level or small level through adders 64 and 65 in accordance with set signals applied by a digital set input 68 through a D-A converter 50 and a medium flaw comparison level input 66 and a small flaw comparison level input 67, whereby when there is for example an input corresponding to a defect smaller than 2 mm deep, an output is generated from the small flaw comparison circuit 48 or 48′, and when there is an input corresponding to a defect greater than 2 mm but smaller than 5 mm deep, an output is generated from the medium flaw comparison circuit 47 or 47′ and at the same time the output of the small flaw comparison circuit 48 or 48′ is cancelled by means of an adder 86 or 86′. In the Figure, numeral 46 designates a recoder for recoding the flaw detection outputs from the two channels and the large flaw signal detection circuit 60 and the gap signal output of the distance detecting circuit 59.

Also in the Figure, the flaw signal from the large flaw signal detection circuit 60 is applied to the similar large flaw signal level comparison circuit 49 and consequently the amplitude of the large flaw signal is compared through an adder 70 in accordance with a set signal applied by a digital set input 72 through a D-A converter 69 and a large flaw comparison level input 71 so as to discriminate defects greater than 5 mm deep. Numerals 61, 62, 61′, 62′ and 63 designate signal delay circuit, so that the delay circuits 61 and 61′ receive the medium flaw outputs from the channels, the delay circuits 62 and 62′ the small flaw outputs from the channels and the delay circuit 63 the large flaw output. The peripheral speed pulses from the pulse generator 76 are applied through a reshaping circuit 77 and marking distance preset circuits 73, 74, 73′, 74′ and 75 to the delay circuits, and consequently when the flaw output is applied to one of the delay circuits, an energization signal is applied to the solenoid of corresponding one of solenoid valves 80, 81, 80′, 81′ and 82 connected respectively to the outputs of the delay circuits 61, 62, 61′, 62′ and 63. In other words, the supply of paint from paint tanks 78y, 78w and 78r to the nozzles 85y, 85w, 85′y, 85′w and 85r, respectively, is controlled by the solenoid valves so that when the flaw signal is applied to the delay circuit, the paint is sprayed after a delay time including a delay time in the operation of the paint supply system and determined in accordance with the round billet peripheral speed measured by the pulse generator 76 and the nozzle to coil distance. In the Figure, the nozzles 85y and 85′y are respectively controlled by the solenoids 80 and 80′ connected to the tank 78y through a pipe line 79y, and consequently the nozzles 85y and 85′y are respectively responsive to the medium flaw outputs from the two channels to respectively spray the yellow marking paint just below the coils 29a, 29b and 29e, 29f, respectively. On the other hand, the nozzles 85w and 85′w are respectively controlled by the solenoid valves 81 and 81′ connected to the tank 78w through a pipe line 79w, and consequently the nozzles 85w and 85′w respectively spray the white marking paint just below the coils 29c, 29d and 29g, 29h in response to the small flaw outputs of the two channels. Similarly, the nozzle 85r is controlled by the solenoid valve 82 connected to the tank 78r through a pipe line 79r, and consequently the nozzle 85r sprays the red marking paint just below the coil 30 in response to the large flaw output. In the Figure, numeral 83 designates a compressed air source for the nozzles, and 84 an air pipe line, whereby compressed air is supplied to the respective nozzles even when there is no supply of paint thereto, and consequently the nozzles always blow air to prevent clogging of the nozzles.

We claim:

1. A surface defect detecting apparatus for cylindrical metal pieces which rotate at a predetermined peripheral speed and move in a lengthwise direction relative to a sensor block comprising, a plurality of eddy-current flaw detecting coils facing the test piece, said sensor block being rotatable about a horizontal axis extending vertically with respect to the axis of said test piece to follow up deflections of said test piece in the direction of the axis of rotation; said sensor block is provided at its front and rear end, viewed in longitudinal direction of said test piece, with a pair of guide wheel means being pressable from above onto said piece to be inspected, said sensor block further comprising color marking means for automatically marking defect areas in response to detector signals depending on the depth of the defect, wherein: relative movement in the longitudinal direction of the test piece is carried out by means of a carriage to which the sensor block is secured, said guide wheels of each pair of guide wheel means are arranged in a plane transverse with respect to the longitudinal direction of the test piece, at a predetermined distance from each other; a base member is suspended from said carriage supported by a supporting girder means, onto which base member pressure is exerted by a presser and to which a slide plate is mounted, said slide plate is slidable in a horizontal direction, vertically with respect to the direction of travel of said carriage, a follow-up plate being resiliently suspended from said slide plate, a sensor holder being suspended from said follow-up plate by means of a resilient means and a hinge for rotation about the horizontal axis, to front and rear parts of which follow-up plate guide wheels are mounted, said sensor holder being adapted to support said eddy current flaw detecting coils, whereby both ends thereof have turning wheels associated therewith; first end positioning table means whereby said material, upon entering, is moved in an axial direction to locate one end of said material in a predetermined position, second table means including a plurality of turning rollers to rotate at the predetermined peripheral speed said material which has been subjected to said end positioning, said carriage being movably mounted on said supporting girder means to permit movement of said carriage while so disposed such that said sensor block suspended from said carriage is positioned just above said second table means, and extractor means movable at right angles to said first and second table means for moving said material to said first table means, moving said material from said first table means to said second table means and further removing said material from said second table means; said eddy current flaw detecting coils are arranged in a line in the longitudinal direction of the test piece in a single sensor holder included within said sensor block at respective front and rear ends of said sensor holder in a longitudinal direction of the test piece, the speed of the travel of the carriage is determined in accordance with the distance between said eddy current flaw detecting coils in said feedback circuit which is dependent on the width of said eddy-current flaw detecting coils, a predetermined set peripheral speed value and the outer diameter of said material, so as to detect the defects of said material; said turning wheel means are each positioned between said guide wheels arranged in the direction of spiral scanning, and in rotatable contact with the outer surface of said test piece, the impedances of the coils are differently selected such that the characteristics of feedback amplifiers form a feedback circuit each with two of said coils are fed by a generator, and are linear for eddy-current signals corresponding to different flaw depth ranges; a phase detector circuit to provide signals in response to different flaw depth range are amplified within the linear characteristic range and are supplied to nozzles of the color marking means, said nozzles each being associated with a flaw depth range, being adapted to spray different colors and said sensor block further comprises an eddy-current distance detecting coil for measuring the gap between said eddy-current flaw detecting coils and the outer surface of said material, and wherein there is further provided automatic gain control means whereby a flaw signal detected by each of said eddy-current flaw detecting coils is subjected to automatic gain control in response to a gap distance signal detected by said distance detecting coil.

* * * * *